United States Patent
Petry et al.

(12) 
(10) Patent No.: US 6,406,858 B1
(45) Date of Patent: Jun. 18, 2002

(54) SYSTEM FOR THE REDUCTION OF INTERFERENCES IN IMMUNOASSAYS

(75) Inventors: Christoph Petry, Krefeld (DE); Richard Bauer, Danbury, CT (US); Alexander Belenky, Holland, PA (US); Sylwia Karwowska, Dobbs Ferry; Henry Mindicino, Monroe, both of NY (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/200,567

(22) Filed: Nov. 27, 1998

(51) Int. Cl.[7] .................................................. G01N 33/53
(52) U.S. Cl. .................... 435/7.1; 435/7.6; 435/7.9; 435/7.92; 435/7.93; 435/7.94; 435/7.95; 435/180; 435/181; 435/184; 435/188; 435/962; 435/964; 436/177; 436/825
(58) Field of Search ...................... 435/7.1, 7.6, 7.9, 435/7.92, 7.93, 7.94, 7.95, 180, 181, 184, 188, 962, 964; 436/177, 825; 530/362, 363, 364

(56) References Cited

U.S. PATENT DOCUMENTS

| | | | | |
|---|---|---|---|---|
| 4,238,565 A | * | 12/1980 | Hornby et al. |
| 4,318,983 A | * | 3/1982 | Hornby et al. |
| 4,582,791 A | * | 4/1986 | Khanna et al. |
| 4,666,831 A | * | 5/1987 | Janoff et al. |
| 4,722,889 A | * | 2/1988 | Lee et al. |
| 4,810,635 A | * | 3/1989 | Ledden et al. |
| 4,914,040 A | * | 4/1990 | Lenz et al. |

OTHER PUBLICATIONS

Mindicino et al., Clin. Chem. 36 (6):1097–1098, 1990.*
Baran et al., Clin. Chem., 33 (6):882, 1987.*
Schwartz et al., Clin. chem., 31 (6):983, 1985.*
Webster's Ninth New Collegiate Dictionary, p. 912, 1990.*

* cited by examiner

*Primary Examiner*—Bao-Thuy L. Nguyen
(74) *Attorney, Agent, or Firm*—Jerome L. Jeffers

(57) ABSTRACT

The present invention is an improvement to the method of determining the concentration of an analyte in body fluid using at least two immunoreactants which specifically bind with separate epitopes of the analyte one of which immunoreactant is immobilized on a solid support and the other is in the form of a polymer or oligomer of the immunoreactant and an enzyme. The improvement involves introducing to the assay system a polymeric conjugate of the enzyme and a water soluble protein other than the enzyme or a non-proteinaceous natural, synthetic or semi-synthetic polymer or oligomer in sufficient amount to reduce bias in the assay due to incorrect recovery of the analyte.

10 Claims, No Drawings

SYSTEM FOR THE REDUCTION OF INTERFERENCES IN IMMUNOASSAYS

BACKGROUND OF THE INVENTION

Due to their particularly high specificity and sensitivity, immunoassays are frequently used for the detection of proteins in serum, plasma, urine or other body fluid samples for medical and diagnostic purposes. Various analytes, such as Thyroid Stimulating Hormone (TSH), Troponin, Prostate Specific Antigen (PSA) or cardiac hormones are detectable with a high degree of sensitivity by sandwich type immunoassays, but for many analytes the requirements for analytical and functional sensitivity are becoming more and more demanding. This is particularly true in the case of TSH because low levels of TSH (around 0.1 $\mu$IU/mL) may be caused by different diseases than very low levels (around 0.01 $\mu$IU/mL). Thus, different therapeutic approaches might be chosen based on a TSH measurement. This requires that the reported TSH result must not be skewed by an immunoassay's imprecision at the low end.

In case of TSH, assays are classified in terms of different generations wherein an assay with a total CV of 20% or better at 1–2 $\mu$IU/mL is called a $1^{st}$ generation TSH Assay. The lowest level of analyte an assay is capable of measuring with an imprecision of 20% is called the assay's functional sensitivity. TSH assays with a functional sensitivity of 0.1 to 0.2 $\mu$IU/mL are called $2^{nd}$ generation and correspondingly assays with a functional sensitivity of 0.01 to 0.02 $\mu$IU/mL are called $3^{rd}$ generation. At this point, $3^{rd}$ generation immunoassays for TSH are regarded as the state of the art.

An effective and commonly applied method for the detection of analytes such as TSH involves the use of a first antibody specific to one epitope on an analyte molecule and a second antibody directed against another epitope on the analyte and labeled with an enzyme or other label which is able to generate a signal. This will allow the formation of a sandwich complex of the two antibodies and the antigen. The first antibody can be directly attached to a solid support or bound thereto through a hapten label, such as a fluorescein derivative which itself is bound to the solid support through an immuno reactant. The sensitivity of such assays is determined by a variety of factors such as the affinity of the antibodies used and the amount of signal generated by the conjugate with the second antibody. One possibility of increasing the sensitivity of such an assay is using a macromolecular conjugate of the enzyme and the second antibody. The binding of such a conjugate by a single analyte molecule provides a much higher signal compared to a conventionally prepared enzyme conjugate since there are several signal generating enzyme molecules present in the formed immune complex. A difficulty with this approach lies in the discovery that the macromolecular nature of the conjugate may lead to a substantially increased avidity for other, non-analyte components in the sample of body fluid being assayed (e.g. serum), which can cause under-recovery of the target antigen in native patient sera.

Sandwich immunoassays are potentially affected by interfering substances (e.g. heterophilic factors, complement, human-anti-mouse-antibodies) that can bridge the capture and detection antibodies or block one of the antibodies resulting in falsely elevated or depressed results. In the case of the approach of enhancing the sensitivity using highly polymerized read-out conjugates as described above, a falsely depressed result, often called under-recovery, can be observed with many patient samples, but is normally not encountered in buffer solutions containing the purified analyte. The source of the under-recovery noted in such an assay using macromolecular enzyme-antibody conjugates is believed to be caused by the binding of one or several serum components to the conjugate to hereby complicate its interaction with the analyte or reduce the turnover of the assay's substrates. For a given sample containing the unknown interferents, the degree of the under-recovery appears to be proportional to the level of polymerization of the enzyme-antibody conjugate used for readout.

In U.S. Pat. No. 4,914,040; there is described a phenomena in which interferents in serum such as rheumatoid factors and anti-Fc immunoglobulins such as IgM lead to misrecovery in immunological sandwich assays due to non-specific binding reactions. This problem can be dealt with by using Fab and F(ab')$_2$ fragments, for one or both of the specific antibodies used in the assay, so that interferents which are directed to the F$_c$ part of IgG lose their point on the specific immune reagents. This reference notes, however, that interferences continue to occur in some human serum immunoassays despite the use of fragments of antibodies in the reagents. The approach described in this patent to combat the interference is to include in the assay a cross-linked immunoaggregate containing an immunocomponent obtained from an animal species different from the species from which the biological fluid is derived at a concentration of from about 0.1 to about 50 $\mu$g/mL of test sample which immunocomplex does not bind with the component to be determined. In a preferred embodiment of this system, the immunoaggregate comprises nonspecific IgG cross-linked to a second macromolecule such as a water soluble protein.

SUMMARY OF THE INVENTION

The present invention is an improvement to the method for the determination of an analyte in a test sample of a biological fluid which method involves contacting the sample with at least two immunoreactants which specifically bind with the analyte and one of the immunoreactants is labeled with an enzyme wherein the conjugate made up by the second antibody and the enzyme is polymeric or oligomeric. The improvement involves the introduction into the assay of a third conjugate of the enzyme which is used to label the immunoreactant and a different water soluble protein or a non-proteinaceous natural, synthetic or semi-synthetic polymer or oligomer. This third conjugate, the scavenger-conjugate, which has to be polymeric with size-exclusion chromatography suggesting a required molecular mass of more than 5,000 kD for an ALP-IgG polymer. It is added to the assay formulation in order to reduce the interaction of the unknown interferents and the enzyme conjugate made from the second antibody and the enzyme used for readout. The effectiveness of the scavenger conjugate results in the presentation of the incorporated enzyme in a manner similar to its presentation in the conjugate with the second antibody. Therefore an effective competition of the scavenger conjugate with the readout conjugate for potentially interfering substances is accomplished. While a polymer made up by the readout enzyme only shows a limited amount of effectiveness, polymers made from only the second component of an effective scavenger conjugate (e.g. Bovine Serum Albumin (BSA), Bovine Gamma Globulin (BGG) or Keyhole Limpet Hemocyanin (KLH) or of copolymers from the second component of the scavenger with fragments of itself as described in U.S. Pat. No. 4,914,040 are completely ineffective. High molecular weight heteroconjugates made from the enzyme and another macromolecular component were observed to exhibit the highest potency in decreasing the effect of the interferents on the recovery of the assay.

DESCRIPTION OF THE INVENTION

The method of the present invention is particularly suitable for the quantitative detection of analytes which must be determined in minute quantities in order to accurately diagnose a possible disease state.

Thus, while TSH is a natural choice for application of this improved assay technique, other analytes such as troponin, PSA and insulin are also well suited to its use in determining their concentration in a sample of body fluid.

As previously mentioned, the immunoreactant which is enzyme labeled to provide a detectable signal upon reacting with the analyte and being contacted with a substrate for the enzyme is in the form of a polymer or oligomer created by the interaction of the immunoreactant and the enzyme. The formation of the polymer or oligomer is accomplished in the same or related manner as the interference suppressing conjugate which is introduced to the assay system. While oligomers will serve to increase the recovery of analyte, high molecular weight polymers which form colloidal solutions are preferred to ensure maximum interaction with and capture of the analyte and increased signal when contacted with a substrate for the enzyme. Typically, the enzyme will be alkaline phosphatase, but other enzymes such as horse radish peroxidase and glucose oxidase can be used if desired.

The polymeric conjugate of the same enzyme used to label the immunoreactant and a water soluble protein (different than the immunoreactant) or non-proteinaceous natural, synthetic or semi-synthetic polymer or oligomer is prepared by chemical crosslinking using homo or hetero bifunctional or multifunctional cross-linkers or by heat aggregation. The selection of the crosslinker does not depend on the class of the second macromolecule (natural or synthetic) but on the nature of the reactive groups on its surface. The following crosslinkers are all directed against amino groups, but other groups such as carboxylic acids, hydroxyl groups or aldehydes are possible crosslinking sites and would require different crosslinkers. For chemical crosslinking, cross-linkers are generally necessary although so called zero-length crosslinkers can be employed that are not incorporated into the conjugate but are rather employed to activate the proteins. With heat induced crosslinking, no crosslinkers are required. The preparation is conducted in the presence of a cross-linker such as N-Succinimidyl (4-iodoacetyl) aminobenzoate (SIAB), Succinimidyl 4[N-maleimidomethyl]-cyclohexane-1-carboxylate (SMCC), 2-Iminothiolane (2IT), glutaraldehyde (GA), Bis(sulfosuccinimidyl) suberate (BS3) or combinations thereof. The cross-linkers are normally used in stoichometric excess (5 to 100 fold) and added to a mixture of the proteins to be cross-linked or to separate solutions of the proteins if multi-step coupling procedures are used as in Example III herein.

Exemplary of water soluble proteins which may be used to form the conjugate are serum albumin; particularly bovine serum albumin; an immunoglobulin such as bovine gamma globulin (BGG), goat IgG or any mouse antibody; keyhole limpet hemocyanin; ovalbumin; and casein and reacting them with the enzyme to form a macromolecular conjugate there is provided a suitable material for reducing or eliminating the interference in the type of assay under consideration which causes under recovery of the sought after analyte. While we do not wish to be bound by any particular theory or mechanism as to how the macromolecular conjugate of the present invention interacts with the assay components to reduce or prevent underrecovery of the analyte, it is believed that it competes with the enzyme conjugate incorporating the second antibody for the interferents present in the biological sample using the same mechanisms of interaction, e.g. van der Waals forces, hydrophobic interaction and hydrogen bonds. The polymeric nature of the blocker increases the avidity of its interaction with interferent compounds. In addition to soluble proteins other materials which will carry reactive groups that allow proper functionalization can be used to form the conjugate with the enzyme. Thus, the use of non-proteinaceous natural, synthetic or semi-synthetic polymers or oligomers can be used in place of proteins. Exemplary of such materials are polylysine, polyasparagine and dextranes which will typically have molecular weights in the range of from 3 to 250 K Daltons.

The enzyme containing scavenger conjugate will typically be treated with heat and/or enzyme inhibitors such as silver, lead or copper salts or be exposed to extreme pH conditions to deactivate the enzyme thereby avoiding false positive results emanating from the enzyme in the conjugate. The conjugate is combined with the other assay reagents in sufficient amount to provide a conjugate concentration of from about 50 to 750 µg/mL with a concentration of at least 150 µg/mL being typical.

The method of practicing the present invention is further illustrated by the following examples:

EXAMPLE I

Preparation 1 of the Scavenger Conjugate Using Homobifunctional Crosslinkers

Bovine gamma globulin (100 mg) and alkaline phosphatase (120 mg) were transferred separately into PBS buffer (50 mM $Na_2HPO_4$, 150 mM NaCl, pH 7.4) and concentrated to about 50 mg/mL using Centricon ultrafiltration devices from Amicon. The concentrations of the solutions were determined spectrophotometrically using UV absorption at 280 nm. The absorption coefficients of the proteins were assumed as $E_{280}^{1\%}=10$ for alkaline phosphatase and $E_{280}^{1\%}=13.6$ for BGG. The appropriate amounts of the solutions were mixed at a protein ratio of 1.1:1 (BGG:ALP, weight vs. weight).

A 10 fold molar excess of an aqueous 10 mM solution of Bis(sulfosuccinimidyl)suberate (BS3, Pierce) was added to the protein mixture as cross-linker. Immediately after this addition, the total protein concentration of the mixture was adjusted to 40 mg/mL by dilution with additional PBS buffer. The mixture was incubated at 25° C. for 90 minutes and then stored overnight at 4° C. The reaction was terminated by adding a 20-fold molar excess of glycine over BS3. The resulting colloidal solution was heavily turbid due to the high molecular weight of the conjugate obtained. The preparation can be used as it is as a blocker in immunoassays or after the alkaline phosphatase activity of the scavenger conjugate has been reduced to lower the assay's background as described in Examples V and VI.

EXAMPLE II

Preparation 2 of the Scavenger Conjugate Using Homobifunctional Cross-linkers

Bovine gamma globulin (100 mg) and 120 mg of alkaline phosphatase were transferred separately into PBS buffer (50 mM $Na_2HPO_4$, 150 mM NaCl, pH 7.4) and concentrated to about 50 mg/mL using Centricon ultrafiltration devices from Amicon. The concentrations of the resulting solution was determined spectrophotometrically using the UV absorption of the solution at 280 nm. Appropriate amounts of the solutions were mixed at a protein ratio of 1.1:1 (BGG:ALP, weight vs weight).

A 25 fold molar excess of an aqueous 25 mM solution of glutaraldehyde (GA) was added to the protein mixture and immediately thereafter the solution's protein concentration was adjusted to 40 mg/mL by dilution with PBS buffer. The mixture was incubated at 25° C. for 90 minutes and then stored overnight at 4° C. after which the reaction was terminated by adding a 20 fold molar excess of glycine over GA. The procedure provides a heavily turbid colloidal solution due to the high molecular weight of the conjugate obtained. The conjugate can be used as it is as a blocker in immunoassays or after the alkaline phosphatase activity of the scavenger conjugate has been reduced to lower the assay's background as described in Example V and VI.

EXAMPLE III
Preparation of the Scavenger-Conjugate Using Heterobifunctional Cross-linkers 100 mg of bovine serum albumin (BSA) were dissolved in TSE85 Buffer (100 mM Triethanolamine, 100 mM Sodium Chloride, 1 mM EDTA, pH 8.5). 200 mg of alkaline phosphatase (ALP) were buffer exchanged into TSE 73 Buffer (100 mM triethanolamine, 100 mM sodium chloride, pH 7.3) using Centricon ultrafiltration devices from Amicon. Both solutions were adjusted to a protein concentration of 50 mg/mL.

A 25 fold molar excess of a 20 mM solution of 2-Iminothiolane (2IT, Pierce) in TSE85 buffer was added to the BSA solution and incubated at 25° C. for 10 minutes. A 25 fold molar excess of a 20 mM solution of Succinimidyl-4-(maleimidomethyl)cyclohexane-1-carboxylate (SMCC, Pierce) in DMSO was added to the alkaline phosphatase solution. After 10 minutes, the activation of BSA and after 20 minutes for the alkaline phosphatase the activation reactions were terminated by adding a 100-fold excess of an aqueous solution of 1 M glycine over each of the crosslinkers (2IT and SMCC). Both activated proteins were purified on Sephadex 25 columns (Pharmacia). For both activated proteins the void volume fraction of the columns was collected and concentrated to 40 mg/mL. During the concentration the buffer of both solutions was changed to TSE73 (100 mM triethanolamine, 100 mM sodium chloride, 1 mM EDTA, pH 7.3). For the concentration and buffer exchange stirring cells from Amicon were used. The protein concentration was determined as described above.

After concentration the proteins were mixed while being stirred on a magnetic-bar stirrer. The reaction was allowed to proceed at room temperature while stirring for 3 hours and was then transferred to a refrigerator (2 to 8° C.) for storage over night. During the reaction the mixture turned heavily turbid due to the formation of a ALP-BSA heteropolymer.

The conjugate can be used as it is as a blocker in immunoassays or after the alkaline phosphatase activity of the scavenger conjugate has been reduced to lower the assay's background as described in Examples V and VI.

EXAMPLE IV
Preparation of the Scavenger Conjugate by Heat Aggregation 100 mg of alkaline phosphatase and 50 mg of BGG were buffer exchanged into PBS74 (50 mM sodium dihydrogen phosphate, 150 mM sodium chloride, pH 7.4) using stirred cells from Amicon. The concentration was adjusted to 5 mg/mL for both solutions. The proteins were mixed in a w/w ratio of 2:1 and heated in a water bath to 75° C. After the internal temperature of the solution had reached 75° C., this mixture was kept at the temperature for 30 minutes. The flask was removed from the water bath and the solution cooled down to room temperature. During the reaction, the mixture turned heavily turbid due to the formation of a ALP-BGG heteropolymer. The enzymatic activity of the scavenger conjugate obtained by this procedure was minimal so that normally there would be no need for an additional deactivation of the enzyme.

EXAMPLE V
Acid Heat Deactivation of the Scavenger Conjugate

A scavenger conjugate solution as obtained in Examples I to III was diluted with a 1 M sodium acetate solution, pH 4.5 to a final concentration of 10 mg/mL. The solution was warmed up in a water bath (65° C.) until it had reached the bath's temperature and was kept at this temperature for an additional 30 minutes. The solution was cooled down to room temperature and the pH was adjusted to 7.0 by the dropwise addition of a 2 M solution of TRIS [Tris (hydroxymethyl)aminomethane] at a pH of 8.8. This procedure resulted in the nearly complete removal of the ALP's enzymatic activity.

EXAMPLE VI
Alkaline Heat Deactivation of the Scavenger Conjugate

The protein conjugates prepared as in Examples I to IV were diluted with 1 M NaHCO$_3$, buffer (pH 9.0) to a final concentration of 10 mg/mL and warmed up in a water bath to 65° C. and was kept there for an additional 30 minutes. The solution was cooled to room temperature and the pH was adjusted to 7.0 by the dropwise addition of a 1.8 M solution of sodium acetate (pH 4.9). This procedure resulted in the basically complete deactivation of the alkaline phosphatase component of the conjugate.

EXAMPLE VII
Preparation of a Polymeric 2nd Antibody Conjugate for Readout 100 mg of high grade alkaline phosphatase were adjusted to a protein concentration of 12 mg/mL using TSMZ73 Buffer (100 mM triethanolamine, 100 mM sodium chloride, 1 mM magnesium chloride, 0.1 mM zinc chloride, pH 7.3). 50 mg of mouse monoclonal anti-TSH antibody were buffer exchanged into TSE85 buffer (100 mM triethanolamine, 100 mM sodium chloride, 1 mM EDTA, pH 8.5). The IgG concentration was set to 40 mg/mL and measured by the solution's absorbance at 280 nm, an extinction coefficient of 13.6 was used.

A 25 fold molar excess of a 100 mM solution of 2-Iminothiolane (2IT, Pierce) in TSE 85 was added to the concentrated IgG solution and incubation at 25° C. for 10 minutes. A 35 fold molar excess of a 20 mM solution of N-succinimidyl(4-iodoacetyl)aminobenzoate (SIAB, Pierce) in DMSO was added to the alkaline phosphatase solution. After 10 minutes, for the activation the IgG solution and after 20 minutes for the alkaline phosphatase solution the activation reactions were terminated by adding a 10-fold excess of an aqueous solution of 1 M glycine over each of the crosslinkers (2IT and SIAB). Both activated proteins were purified on Sephadex G-25 columns (Pharmacia). For both activated proteins the void volume fraction of the columns was collected and concentrated to 25 mg/mL. During the concentration the buffer of both solutions was changed to TSE83 (100 mM triethanolamine, 100 mM sodium chloride, 1 mM EDTA, pH 8.3). For the concentration and buffer exchange stirring cells from Amicon were used. The protein concentration was determined as described above.

After concentration the proteins were mixed while being stirred on a magnetic-bar stirrer. The reaction was allowed to proceed at room temperature while stirring for 3 hours and was then transferred to a refrigerator (2 to 8° C.) for storage over night. During the reaction the mixture turned turbid due to the formation of a IgG-ALP heteroconjugate.

The product formed was purified using FPLC equipment from Pharmacia on a Superose 6 column. The elution profile of the conjugate reveals that a significant portion of the conjugate is eluting in the void volume of the column and that there is only little of unreacted material left. For the purpose of running the TSH immunoassay all fractions with the exception of the unreacted starting material were selected.

EXAMPLE VIII

Applicantion and Utility of the Scavenger Conjugate $3^{rd}$ generation TSH immunoassay was designed employing a polymeric tag conjugate as described in Example VII. The capture antibody was made from a fluorescein isothiocyanate labeled anti-TSH F(ab')$_2$ fragment that can bind to magnetic particles through antifluorescein antibodies. The immuno complex formed by the presence of TSH in a serum sample added to the assay reagents is precipitated by the magnetic particles. The oligomeric alkaline phosphatase conjugate was used at a concentration of 24 mg/L, the fluoresceinated F(ab')$_2$ was used at 2 mg/L. The assay was run on the Bayer Immuno 1® system.

In this configuration, the assay showed an under recovery with more that 10% of serum samples from a random collection. In the following Table I, the effect of the scavenger conjugates (300 mg/L) on analyte detection is compared to reagents not containing any scavenger conjugate.

TABLE I

| linker used in the blocker conjugate serum sample used | BS3 | GA | SMCC/ 2IT | No Scavenger Added |
|---|---|---|---|---|
| | | | TSH [μU/mL] | |
| XS15566 | 1.59 | 1.76 | 1.2 | 0.89 |
| ZT47462 | 1.12 | 1.86 | 1.44 | 0.88 |
| PT33937 | 1.04 | | 0.97 | 0.73 |
| MT52224 | | | 1.47 | 1.07 |
| BT57383 | 4.14 | 4.55 | 4.80 | 3.0 |

In a random selection of 302 bloodbank samples the correlation of the assay with and without scavenger against a second TSH method yielded the following results as set out in Table 2:

TABLE 2

| | With Scavenger Conjugate | Without Scavenger Conjugate |
|---|---|---|
| Slope | 1.00 | 0.94 |
| Intercept | −0.05 | −0.06 |
| r$^2$ (coefficient of correlation) | 0.99 | 0.98 |
| Count | 300 | 302 |

From Table 2 it can be determined that the addition of the scavenger conjugate leads to an average recovery improvement of 6% in a random selection of 300 samples. This is mainly achieved by eliminating low outliers. The reduced scatter in the correlation is reflected by an increase of r$^2$ from 0.98 to 0.99.

What is claimed is:

1. In a method for determining an analyte in a sample of biological fluid which comprises forming a mixture by contacting the sample with at least two immunoreactants which specifically bind with the analyte; one of said immunoreactants is conjugated to an enzyme, said conjugate comprising several or multiple molecules of said immunoreactant and several or multiple molecules of said enzyme, the improvement comprising:

a) further combining the above mixture with a crosslinked scavenger conjugate which functions to reduce interfering substances which may be present in the sample, the scavenger conjugate comprising a polymeric conjugate of an enzyme and a water soluble molecule selected from the group consisting of a water soluble protein which is different from the above immunoreactants, a non-proteinaceous natural polymer, a non-proteinaceous natural oligomer, a non-proteinaceous semi-synthetic polymer, and a non-proteinaceous semi-synthetic oligomer, wherein the enzyme used in the cross-linked scavenger conjugate is the same as the enzyme conjugated to the immunoreactant;

b) detecting any complexes formed between the immunoreactants and the analyte; and c) correlating any detected complexes with the presence of analyte in the sample.

2. The method of claim 1 wherein the enzyme is selected from the group consisting of alkaline phosphatase, horse radish peroxidase and glucose oxidase.

3. The method of claim 2 wherein the enzyme is alkaline phosphatase.

4. The method of claim 3 wherein the cross-linked scavenger conjugate comprises a polymer selected from the group consisting of serum albumin, an immunoglobulin and keyhole limpet hemocyanin.

5. The method of claim 1 wherein the immunoglobulin is selected from the group consisting of bovine gamma globulin, goat IgG and a mouse antibody.

6. The method of claim 1 wherein the analyte is selected from the group consisting of thyroid stimulating hormone, prostate specific antigen and insulin.

7. The method of claim 6 wherein the analyte is thyroid stimulating hormone.

8. The method of claim 1 wherein the concentration of the cross-linked scavenger conjugate in the mixture is from 50 to 750 μg/mL.

9. The method of claim 8 wherein the concentration of the cross-linked scavenger conjugate in the mixture is greater than 100 μg/mL.

10. The method of claim 1 wherein the biological fluid is selected from the group consisting of mammalian serum, plasma, urine, saliva and spinal fluid.

* * * * *